United States Patent [19]
Stavrianopoulos

[11] Patent Number: 5,989,809
[45] Date of Patent: Nov. 23, 1999

[54] METHODS FOR DETECTING A POLYNUCLEOTIDE USING AN INACTIVATING REAGENT AND COMPOSITION AND KIT COMPRISING SAME

[75] Inventor: Jannis G. Stavrianopoulos, New York, N.Y.

[73] Assignee: Enzo Diagnostics, Inc., Farmingdale, N.Y.

[21] Appl. No.: 08/378,118

[22] Filed: Jan. 24, 1995

Related U.S. Application Data

[63] Continuation of application No. 07/633,730, Dec. 24, 1990, abandoned.

[51] Int. Cl.$^6$ .............................. C12Q 1/68; C07H 21/00
[52] U.S. Cl. ........................... 435/6; 536/24.3; 536/25.32
[58] Field of Search ..................... 435/6, 91.1; 536/24.3, 536/25.32

[56] References Cited

FOREIGN PATENT DOCUMENTS

| | | |
|---|---|---|
| 0231495 | 8/1987 | European Pat. Off. . |
| 0309230 | 6/1995 | European Pat. Off. . |
| 1295153 | 4/1962 | France . |
| 1203781 | 10/1965 | Germany . |
| 901643 | 7/1962 | United Kingdom . |
| 931227 | 7/1963 | United Kingdom . |
| 8902476 | 3/1989 | WIPO . |

OTHER PUBLICATIONS

Bhavsar, et al., "Synthesis of Acridine Derivatives", 107 *Chemical Abstracts*, 667 (Abstract No. 96576U) 1987.
Arnold et al. Clin. Chem. 35 1588–1594 (1989) Assay Formats Involving Acridinium–Ester–Labeled DNA Probes.
Morrison et al. "Organic Chemistry" Allyn and Bacon, Inc. Boston (1973) pp. 765–775.

*Primary Examiner*—John S. Brusca
*Attorney, Agent, or Firm*—Ronald C. Fedus, Esq.

[57] ABSTRACT

The present invention provides a method for detecting the presence of a target polynucleotide in a sample. The method comprises the steps of (a) contacting the sample under hybridizing conditions with (i) a single-stranded polynucleotide probe capable of hybridizing to the target polynucleotide and comprising a polynucleotide and at least one intercalating molecule attached to a nucleotide of the polynucleotide by means of a linker arm, and (ii) a background-reducing reagent which chemically modifies the intercalating molecule when the probe to which it is attached is single-stranded; and (b) detecting a property change resulting from the intercalation of the intercalating molecule into a target-probe hybrid, thereby detecting the target polynucleotide. The intercalating molecule which is part of the polynucleotide probe induces a change in a property, in either the probe, the target polynucleotide or a target-probe hybrid. The property change can be detected, for example, by means of a generated signal which can be identified or quantified. The present invention can be employed in a heterogeneous (two step or two phase) assay using a support to immobilize the target or probe, and a washing step, and in a homogeneous (one step or one phase) assay using a hybridization solution. Also provided are a composition and a nucleic acid hybridization kit useful for detecting the presence of a target polynucleotide in a sample.

50 Claims, No Drawings

METHODS FOR DETECTING A POLYNUCLEOTIDE USING AN INACTIVATING REAGENT AND COMPOSITION AND KIT COMPRISING SAME

CROSS-REFERENCE TO RELATED APPLICATIONS

This application is a continuation of U.S. patent application Ser. No. 07/633,730, filed Dec. 24, 1990, now abandoned.

This invention provides a method for detecting the presence of a target polynucleotide in a sample by employing a background reducing reagent which reduces the signal generated by unhybridized background material. This invention also provides a composition and a nucleic acid hybridization kit using such a background reducing reagent.

All patents, patent publications and literature references cited in this specification are hereby incorporated by reference in their entirety in order to describe more fully the state of the art to which this invention pertains.

BACKGROUND OF THE INVENTION

Polynucleotide hybridization assays using a polynucleotide probe for verifying the presence of a target polynucleotide analyte are well known in the art. Hybridization is based on complementary base-pairing between target and probe sequences. The quantity of the polynucleotide probe, as compared to the target polynucleotide, is in excess with ratios of 6:1 of probe per target, or greater being employed conventionally. Furthermore, the amount of the probe which hybridizes to the target is typically a fraction, 0.1%. Therefore, it is very desirable to quench the fluorescence of the unhybridized probe so that minute quantities of the polynucleotide probe hybridized to the target can be accurately detected.

In U.S. application Ser. No. 06/808,757, now abandoned, a homogeneous assay method is disclosed in which a polynucleotide probe is used to detect the presence of a target polynucleotide in a sample. Much of the contents of U.S. application Ser. No. 06/808,757, now abandoned has already been published. See, e.g., corresponding European Patent Application Publication No. 231,495, published on Aug. 12, 1987.

The disclosed probe comprises a polynucleotide and at least a first entity and a second entity. The first entity is attached to a first nucleotide of the polynucleotide by means of a linker arm, separated by about ten nucleotides from the second entity which is attached to a second nucleotide, also by means of a linker arm. Upon hybridization of the probe to the target polynucleotide, the entities, by virtue of their characteristics, e.g., the ability to intercalate into a target-probe hybrid, provide for a property change in either the probe, the target, or both. The change in property can be detected by appropriately measuring an associated signal, e.g., radiation emission, interaction of molecular dispersion forces, such as melting temperature, and buoyant density.

It has now been discovered that the signal intensity in a hybridization assay can be significantly enhanced by contacting the hybridization reaction mixture with a background-reducing reagent which chemically modifies the intercalating groups, e.g., of an aromatic dye, when the probe to which these intercalating groups are attached remains unhybridized to target. By modifying the intercalating groups in this way, interfering signal from the unhybridized single-stranded probe can be reduced significantly, if not altogether eliminated.

SUMMARY OF THE INVENTION

The present invention provides a method for detecting the presence of a target polynucleotide in a sample. The method comprises the steps of (a) contacting the sample under hybridizing conditions with (i) a single-stranded polynucleotide probe capable of hybridizing to the target polynucleotide and comprising a polynucleotide and at least one intercalating molecule attached to a nucleotide of the polynucleotide by means of a linker arm, and (ii) a background-reducing reagent which chemically modifies the intercalating molecule when the probe to which it is attached is single-stranded: and (b) detecting a property change caused by the intercalation of the intercalating molecule into a target-probe hybrid, thereby detecting the target polynucleotide. The intercalating molecule which is part of the polynucleotide probe induces a change in a property in either the probe, the target polynucleotide or a target-probe hybrid. The property change can be detected, for example, by a signal which can be identified or quantified.

The present invention provides a composition comprising a single-stranded polynucleotide probe having at least one moiety with the structure

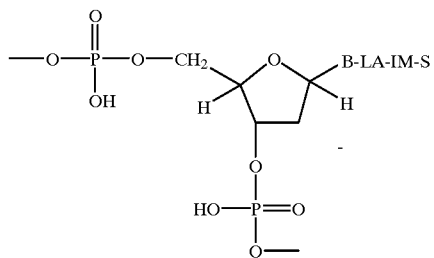

wherein B represents a base selected from the group consisting of pyrimidines, purines and deazapurines, provided that whenever B comprises a pyrimidine, the sugar in the base is attached to the $N^1$-position of the pyrimidine, and whenever B is a purine or a deazapurine, the sugar is attached to the $N^9$-position of the purine or deazapurine. As depicted in the above structure, IM represents an intercalating molecule, LA represents a linker arm comprising at least three carbon atoms and is attached covalently or noncovalently to the intercalating molecule and S represents a background-reducing reagent which modifies the intercalating molecule when the probe attached thereto is single-stranded.

A nucleic acid hybridization kit for detecting the presence of a target polynucleotide in a sample is also provided by the present invention. The kit comprises in one or more containers (1) a single-stranded polynucleotide probe capable of hybridizing to the target polynucleotide, and comprising a polynucleotide and at least one intercalating molecule attached to a nucleotide of the polynucleotide by means of a linker arm. The intercalating molecule induces a change in a property in either said probe, said target polynucleotide or a target-probe hybrid, which property change can be detected, e.g., identified or quantified through a generated signal. The kit also comprises (2) a background-reducing reagent which modifies the intercalating molecule when the probe to which the intercalating molecule is attached is single-stranded. As an optional component, the kit comprises (3) an inactivator which renders the background-reducing reagent inactive so that no further modification of the intercalating molecule can occur.

DETAILED DESCRIPTION OF THE INVENTION

The present invention provides a method, a composition and a hybridization kit for detecting the presence of a target polynucleotide in a sample. As used herein, the term "sample" refers to those materials on which tests are performed, and includes biological, physiological, industrial, environmental and other types of solids and liquids. Of particular interest are biological tissues, such as organ or musculoskeletal specimens or biopsies, cervical and peritoneal specimens or lavages and the like, and fluids, such as serum, plasma, urine, cerebrospinal fluid, saliva, milk, broth, and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluids which are tested by conventional methods are also encompassed by this term and can be assayed in accordance with the invention.

The terms "target polynucleotide" or "target" refer to any nucleic-acid containing substance whose presence or absence is to be qualitatively or quantitatively determined in a sample. The method of the present invention can be applied to the detection of target oligo- or polynucleotides (or a portion thereof) which are at least partially present in single-stranded form or can be made at least partially single-stranded. The analyte, in functional terms, is usually selected from a naturally occurring or synthetic RNA or DNA for which a complementary nucleic acid exists or can be prepared.

The terms "polynucleotide probe" or "probe" refer to any nucleic acid-containing compound or composite capable of recognizing a particular nucleic acid sequence in preference to other substances. In the majority of embodiments, the probes will be DNA hybridization assay oligo- or polynucleotide probes, such as those specific for disease-causing organisms. For examples of such probes, see the product catalog for Enzo Diagnostics, Inc., an Enzo Biochem Company, 1988.

The terms "linker arm," "linkage group," "linker" and the like refer to any of the well known bonds or compounds useful in joining functional groups and which do not substantially interfere with the characteristic properties or functions of the functional groups so joined. Examples of linker arms useful in the present invention include those described for this purpose in Ward et al., U.S. Pat. No. 4,711,955; Stavrianopoulos, U.S. Pat. No. 4,707,352; and Stavrianopoulos, U.S. Pat. No. 4,707,440, as well as pending U.S. application Ser. No. 07/394,284, now abandoned.

The terms "intercalating molecule," "intercalator," "intercalating dye," "intercalating agent" and the like refer to those species, which in the presence of double-stranded polynucleotides, can position themselves between two adjacent base-pairs in the double strands, and further interact with the base-pairs of the double strand. The hybrids can be DNA/DNA, DNA/RNA, or RNA/RNA. The characteristic of the intercalating molecule or agent is its ability to intercalate into a polynucleotide hybrid, such as a hybrid formed between a target polynucleotide and a polynucleotide probe.

Generally, the intercalating agents are aromatic dyes. In order to intercalate into the double strands, these compounds require at least five conjugated bonds. These intercalating aromatic dyes have a planar ring structure and a distinct radiation emission, e.g., fluorescence, spectra. The emission, e.g., fluorescence emission, is indicative of the electron delocalization of the intercalating agent, and is affected by the inductive effect of substituent groups attached to the dye and by quenching agents. For a further discussion of intercalation and intercalating drugs and dyes, see *Principles of Nucleic Acid Structure*, Saenger, W., Springer-Verlag, Charles Cantor editor, New York, 1983, chapter 16, pp. 350–367.

When the intercalating molecule is dissolved in an aqueous or aqueous/organic solution, it is believed that the water in the solution significantly quenches the fluorescence of the dissolved intercalating molecule by raising the ground-energy-state of the molecule to a level higher than when the molecule is in an organic medium. If the intercalating molecule intercalates into a polynucleotide hybrid, the molecule becomes shielded from the water. Shielding occurs because the hybrid contains a relatively hydrophobic interior (the bases) and a hydrophilic exterior (the phosphates). Water thus aggregates at the exterior of the hybrid, and not at the interior. Because the fluorescence emission of the intercalating molecule is no longer quenched by the water, the ground-energy-state shifts to a lower energy level, and the result is that the fluorescence emission maximum shifts to a longer wavelength. The fluorescence intensity of the intercalating molecule, upon intercalation, is also enhanced many fold. This shift in fluorescence emission and intensity is thus a property change that is generated by the intercalating molecule only upon hybridization of the polynucleotide portion of the polynucleotide probe to the target polynucleotide.

As described in U.S. application Ser. No. 06/808,757, now abandoned, a single-stranded polynucleotide probe comprising a polynucleotide and at least one intercalating molecule attached to a nucleotide can be employed to detect a target polynucleotide in a homogeneous or one-step assay. Upon hybridization of the polynucleotide portion of the polynucleotide probe to the target polynucleotide to form a target-probe hybrid, the intercalating molecule intercalates into a groove of the thus formed target-probe hybrid in between stacked base-pairs. This intercalation results in a shift in the fluorescence emission and intensity of the intercalating molecule.

The term "background-reducing reagent" refers to that class of compounds which are capable of chemically modifying the above-described intercalating molecule when the polynucleotide probe to which it is attached is in single-stranded form, i.e., unhybridized to any target polynucleotide. By modifying the intercalating molecule in this way, the background-reducing reagent minimizes or substantially eliminates any interfering signal which might be generated by the unhybridized single-stranded DNA probe labeled with the intercalating (but not intercalated) molecule.

The present invention provides a method for detecting the presence of a target polynucleotide in a sample comprising the steps of: (a) contacting said sample under hybridizing conditions with (i) a single-stranded polynucleotide probe capable of hybridizing to said target polynucleotide, said probe comprising a polynucleotide and at least one intercalating molecule attached to a nucleotide of said polynucleotide by means of a linker arm, wherein said intercalating molecule induces a change in a property in either said probe, said target polynucleotide or both, and (ii) a background-reducing reagent which chemically modifies said intercalating molecule when the probe attached thereto is single-stranded; and (b) detecting said property change, thereby detecting said target polynucleotide. The method can also be carried out by treating the target polynucleotide in the sample so as to render it in substantially single-stranded form prior to contacting the sample with the polynucleotide probe.

In another aspect of this method, a further step of adding an inactivator to the hybridizing reaction mixture can be performed which will render the background-reducing reagent inactive prior to detection of the property change. The inactivator works in the following manner in accordance with the present invention. The intercalating molecule is always in equilibrium between being bound to the double helix and in free form outside of the double helix. In the case where the intercalating molecule is outside of the double helix, it will be inactivated by the background-reducing reagent. To prevent a decrease in the signal e.g., fluorescence, due to reaction with the background-reducing reagent, and because the reaction of the reagent with the unbound ethidium (not Intercalated) is a very fast reaction, it is useful after a certain period of time following hybridization to inactivate the background-reducing reagent. This is achieved by reacting it with a primary amine which forms a linear triazine, or using a diazo compound in the case of aromatic amines, or phenols which form diazo compounds. Merely by way of example, the inactivator can be selected from any of the group consisting of aliphatic primary amines, an aromatic phenol and an aromatic amine, or a combination of any of the foregoing. Among the aliphatic primary amines suitable as inactivators are the following: glycine, alanine, arginine, asparagine, aspartic acid, cysteine, cystine, glutamic acid, glutamine, histidine, hydroxylysine, isoleucine, leucine, lysine, methionine, serine, threonine and valine, or a combination of any of the foregoing. All of these amines are widely available from a number of commercial sources. Preferred as an inactivator in this invention is glycine and histidine. Among suitable inactivators selected from phenols and aromatic amines are aniline, phenol and naphthol.

The property change which results from intercalation of the double-stranded nucleic acid by the intercalating molecule takes a number of diverse forms. For example, the radiation emission of the hybrid will change as a result of intercalation. A particularly useful feature in this respect is radiation emission in the form of fluorescence, which can be conventionally measured using, for example, fluorometers which are widely available in the art. Among other changes in property which occur as a result of intercalation are interactions of molecular dispersion forces, buoyant density, melting temperature, and helical length, or a combination of any of the foregoing property changes. Especially preferred property changes are those which generate a detectable signal, e.g., fluorescence.

It is not always necessary in practicing the present invention to bind the intercalating molecule to the polynucleotide probe. If an assay is being performed using both single-stranded target or sample and a single-stranded polynucleotide probe, the intercalating molecule need not be bound to the probe. Instead a free form of the intercalating molecule could be used, which would intercalate into any target-probe hybrid.

Intercalating molecules useful in the practice of the present invention comprise a number of compounds. These intercalating compounds include, for example, aromatic dyes selected from phenanthridines, acridines and anthrocyclines, or combinations thereof. Useful and even preferred phenanthridines include ethidium, propidium, dimidium and phenidium, or combinations thereof. All are commercially available or can be manufactured using known methodology. Preferred is ethidium, available, for example from Sigma. St. Louis, Mo. When a diazonium salt is added to ethidium, e.g., ethidium bromide, there are four possible points of attack by the diazonium salt as shown below:

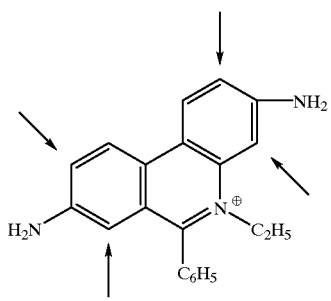

Suitable members from the propidium group of compounds include, by way of illustration, 5-(4'-thiobutyl)-3,8-diamino-6-phenylphenanthridine and 5-(3'-thiopropyl)-3,8-diamino-6-phenylphenanthridine, or a combination thereof. Both are available from commercial sources, e.g., Enzo Biochem, Inc., New York, N.Y. Among the acridine compounds useful in the practice of the present invention is acridine orange, available commercially, for example, from Fisher Chemicals, Fairlawn. N.J.

The intercalating molecule is attached to at least one nucleotide in the polynucleotide probe by means of a linker arm. described above in U.S. Pat. Nos. 4,711,955; 4,707,352; and 4,707,440, supra. The linker arm is typically attached to a base moiety of the polynucleotide probe, although other points of attachment can be used. The base can be selected from the group consisting of purines, pyrimidines and deazapurines, or combinations thereof. In the case of purines, these can comprise adenine or guanine. The linker arm is attached to the 8-position or exocyclic 6-amino position when the purine comprises adenine, or to the 8-position when the purine comprises guanine. Where the base comprises a deazapurine, the linker arm can be attached to the 7 or 8-position of the base. Furthermore, in the case of pyrimidines, these comprise uracil or cytosine. The linker arm is usually attached to the 5 or 6-position when the pyrimidine comprises uracil, or at the 5, 6, or exocyclic 4-amino position when the pyrimidine comprises cytosine. In other embodiments, the linker arm comprises at least 3 carbon atoms and further comprises a double bond at an alpha position relative to the base. By way of example, the linker arm can be selected from any of the following structures:

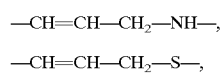

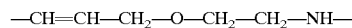

and

—CH=CH—CH₂—O—CH₂—CH₂—NH—

Preferred is the case where the linker arm comprises allylamine, especially where the allylamine is attached to the 5-position of uracil.

The linker arm can be attached to the base moiety in one fragment, or it can be synthesized by first attaching a first fragment to the base, and then attaching a second fragment to the first fragment. Such fragments are described in the aforementioned U.S. application Ser. No. 06/808,757, now abandoned.

Compounds which can be used as background-reducing reagents in accordance with the instant invention include a number of members which comprise the diazonium salts. Suitable diazonium salts are the following: 4-nitrobenzenediazonium salts and derivatives thereof. Preferred is 4-nitrodiazonium salt. In other preferred aspects, the 4-nitrodiazonium salt can be halogen substituted, for example, by chlorine or bromine, or a combination thereof. In the case where the diazonium salt is chlorine substituted, especially useful are the following: 3-chloro-4-nitrobenzenediazonium salt, 3,5-dichloro-benzenediazonium salt, 2,6-dichloro-benzenediazonium salt, 2,3,5,6 -tetrachloro-benzenediazonium salt, 3,5,6-trichloro-benzenediazonium salt, 2,3,5-trichloro-benzenediazonium salt and 2,3,6-trichloro-benzenediazonium salt, or a combination of any of the foregoing. These derivatives can be prepared by reducing 4-nitroaniline (available from Aldrich Chemicals, Milwaukee, Wis.) to an amine and subsequent diazotization with nitrous acid in aqueous (50%) DMSO.

This invention further provides a method for detecting the presence of a target polynucleotide in a sample comprising the steps of: a) contacting the target polynucleotide with (i) a single-stranded polynucleotide probe, which probe comprises a polynucleotide and at least a first intercalating molecular entity and a second intercalating molecular entity. The first intercalating molecular entity is attached to a first nucleotide of the polynucleotide by means of a first linker arm, and the second intercalating molecular entity is attached to a second nucleotide by means of a second linker arm. The first and said second nucleotides are separated by a number of nucleotides sufficient for the provision of target specificity to the polynucleotide. The intercalating molecular entities induce upon hybridization of the polynucleotide probe to the target polynucleotide, a change in a property either in the polynucleotide probe, in the target polynucleotide, or in both. The contacting step also includes the addition of (ii) a background-reducing reagent which chemically modifies the intercalating molecular entities when the probe attached thereto is single-stranded. The method further comprises b) forming a hybrid comprising the polynucleotide probe and the target polynucleotide: and c) detecting the presence of the target polynucleotide by means of the property change. Further embodiments of the components and elements used in the aforementioned method are described earlier in this application, or are described in U.S. application Ser. No. 06/808,757, now abandoned.

The method described in this invention can be employed in both heterogeneous (two phase or two step) assays and homogeneous (one phase or one step) assays. In the case of the former, a solution of the polynucleotide probe bound with the intercalating molecule is added onto a solid support to which the sample or target polynucleotide has been attached. Following hybridization between the probe and target, the support is washed to further remove any unhybridized probe, and thereafter, the background reducing reagent is added to "kill" fluorescence from the non-hybridized probe. This can be followed by further washing, if desired, or washing can be eliminated altogether. In any case, in the two phase reaction system, following hybridization between target and probe, the excess probe with the intercalating (but not intercalated) molecule bound thereto is inactivated (quenched) by the addition of the background-reducing reagent. After washing, signal intensity, or some other property change is determined, which indicates the presence of target. Alternatively, the polynucleotide probe with the attached intercalating molecule can be fixed to a solid support, and a solution containing the target polynucleotide can be added to the support to effectuate hybridization between the target and probe. The background-reducing reagent can then be added to the support shortly after hybridization between the probe and any target contained in the sample.

It has been found that when an intercalating molecule, such as ethidium bromide, is attached to a single-stranded polynucleotide probe, there is a significant enhancement in signal generation, measured conveniently as fluorescence, over the free ethidium unbound in solution after a background-reducing reagent is added to the reaction solution. Moreover, it has been found that when the ethidium is bound and intercalated into double-stranded DNA, there is a further significant enhancement of signal, using a background-reducing reagent in accordance with this invention. Taking these two observations together, it Is estimated that by employing a background-reducing reagent to chemically modify an intercalating molecule attached to a single-stranded polynucleotide probe, the decrease in interfering signal from non-specific material, e.g., unhybridized single-stranded probes, can be as high as 10,000 over the conventional assay.

The present invention provides a composition comprising a single-stranded polynucleotide probe having at least one moiety with the structure

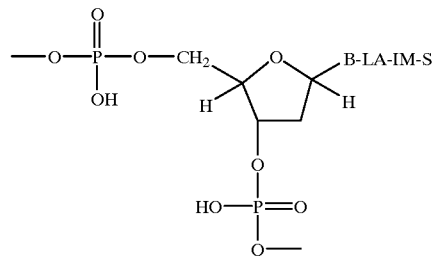

wherein B represents a base selected from the group consisting of pyrimidines, purines and deazapurines, provided that whenever B comprises a pyrimidine, the sugar in the base is attached to the $N^1$-position of the pyrimidine, and whenever B is a purine or a deazapurine, the sugar is attached to the $N^9$-position of the purine or deazapurine. Furthermore, in the above composition, IM represents an intercalating molecule, LA represents a linker arm comprising at least three carbon atoms and is attached covalently or non-covalently to the intercalating molecule, and S represents a background reducing reagent which modifies the intercalating molecule when the probe attached thereto is single-stranded. All of these moieties in the above composition have been described hereinabove.

The present invention further provides a nucleic acid hybridization kit for detecting the presence of a target polynucleotide in a sample. The kit comprises in one or more containers or in packaged combination the following: (1) a single-stranded polynucleotide probe which is hybridizable to the target polynucleotide. The probe comprises a polynucleotide and at least one intercalating molecule attached to a nucleotide of the polynucleotide by means of a linker arm.

The intercalating molecule induces a change in a property in either the probe, the target polynucleotide or both: and (2) a background-reducing reagent which modifies the intercalating molecule when the probe attached thereto is single-stranded. Optionally included in this kit Is (3) an inactivator which renders the background-reducing reagent inactive. The components and elements of this kit have been described hereinabove.

The examples which follow are set forth to illustrate various aspects of the present invention but are not intended to limit in any way its scope as more particularly set forth in the claims.

EXAMPLE 1
Comparison of Emission Between Single-Stranded DNA Bound with Ethidium Bromide and an Intercalated DNA/RNA Hybrid In this example, a comparison was made in terms of fluorescence emission between single-stranded DNA containing intercalated molecules and a double-stranded DNA/RNA hybrid. A standard DNA solution was formulated (10 OD/260 nm) which contained 30 mer thymidine in which every fourth nucleotide was labeled with ethidium bromide. 20 ul from the solution was removed and combined with 0.1 molar sodium acetate buffer at pH 7.0. 5 ul of 0.1 molar diazonium salt prepared by conventional methodology. The diazonium salt was prepared from 4-nitroaniline (Aldrich Chemicals, Milwaukee, Wis.) which was reduced to the corresponding amine, and subsequently diazotized with nitrous acid in 50% (aqueous) DMSO. The reaction was allowed to proceed for five minutes after which time fluorescence was measured under an ultraviolet lamp using a UV lamp from UVP, Inc., San Gabriel, Calif. 91778. Alternatively, fluorescence could be measured with a fluorimeter, e.g., Perkin-Elmer, South Plainfield, N.J., if equipped with the proper UV lamp. Fluorescence in the reaction mixture was observed to disappear during the five minute waiting period.

20 ul from the same standard DNA solution was taken, placed in 0.1 molar sodium acetate buffer (pH 7.0) and combined with an equivalent molar amount of polyribonucleic (polyA) acid. 5 ul of the 0.1 molar diazonium salt used in the first part of this example was then added to the reaction mixture. Reaction was allowed to proceed for five minutes after which time fluorescence was observed to persist in the reaction mixture.

The results of this example demonstrate that intercalation of ethidium bromide into a double-stranded nucleic acid prevents chemical modification by the diazonium salt. The protection of the intercalating molecule by the double-stranded nucleic acid is evidenced by the persistence of fluorescence in the reaction mixture containing the diazonium salt and the double-stranded DNA/RNA hybrid where the ethidium bromide of the DNA strand intercalates into the double helix. Another class of compounds which intercalates into double-stranded helices are the acridines. Acridine orange was used in this next example to investigate the behavior of this particular aromatic dye against the reaction with a background-reducing reagent.

EXAMPLE 2
Comparison Between Double-Stranded DNA Intercalated with Acridine Orange and Unbound Acridine Orange (Free in Solution)

In this example, acridine orange was employed as an intercalating molecule to illustrate the differences between the unbound intercalating molecule (free in solution) and double-stranded DNA which is intercalated with the molecule.

0.1 mg per ml of calf thymus double-stranded DNA was combined with traces of acridine orange (in sodium acetate buffer, pH 7.0). The acridine orange was obtained from Fisher Chemicals, Fairlawn, N.J. After the addition of the acridine, an intensive yellow fluorescence appeared in the reaction mixture.

As a control, a tube was set up without the aforementioned DNA using traces of acridine orange in sodium acetate buffer, pH 7.0. To the buffered solution was added 5 ul of 0.1 molar of the diazonium salt, p-nitrobenzenediazonium chloride, which was prepared by reducing 4-nitroaniline (Aldrich Chemicals, Milwaukee, Wis.) to an amine and subsequent diazotization with nitrous acid in aqueous 50% DMSO.

Reaction was allowed to proceed for five minutes and fluorescence was observed in the reaction solution. After the addition of the diazonium salt, the fluorescence control disappeared, in contrast to the DNA containing solution where the fluorescence persisted. These observations indicate that as an intercalating molecule, acridine orange is protected by the double-stranded DNA, and hints to the wide application of diazonium salts with fluorescent intercalators.

What is claimed is:

1. A method for detecting the presence of a polynucleotide of interest comprising the steps of:
   (a) contacting under hybridizing conditions a sample suspected of containing said polynucleotide of interest with (i) a single-stranded polynucleotide probe capable of hybridizing to said polynucleotide of interest, said probe comprising a polynucleotide and at least one intercalating aromatic dye attached to a nucleotide of said polynucleotide by means of a linker arm, where said intercalating aromatic dye induces a change in a property in either said probe, said polynucleotide of interest, or both, and (ii) an inactivating reagent that chemically modifies and inactivates said intercalating aromatic dye when the probe attached thereto is single-stranded; and
   (b) detecting said property change, thereby detecting said polynucleotide of interest;

wherein said intercalating aromatic dye is selected from the group consisting of phenanthridine, acridine and a combination thereof, said inactivating reagent comprises a diazonium salt, and said property change is a change in radiation emission.

2. The method of claim 1 wherein said polynucleotide of interest is in double-stranded form and said method further comprises the step of rendering said polynucleotide of interest in substantially single-stranded form prior to said contacting step.

3. The method of claim 1 wherein said property change comprises a signal.

4. The method of claim 3 wherein said property change comprises radiation emission.

5. The method of claim 4 wherein said radiation emission comprises fluorescence emission.

6. The method of claim 1 wherein said aromatic dye is a phenanthridine.

7. The method of claim 6 wherein said phenanthridine is selected from the group consisting of ethidium, propidium, dimidium and phenidium, or a combination of any of the foregoing.

8. The method of claim 7 wherein said propidium is selected from the group consisting of 5-(4'-thiobutyl)-3,8-diamino-6-phenylphenanthridine and 5-(3'-thiopropyl)-3,8-diamino-6-phenylphenanthridine, or a combination thereof.

9. The method of claim 6 wherein said phenanthridine comprises ethidium.

10. The method of claim 1 wherein said acridine comprises acridine orange.

11. The method of claim 1 wherein said linker arm is attached to a base moiety of said polynucleotide probe.

12. The method of claim 11 wherein said linker arm comprises at least 3 carbon atoms.

13. The method of claim 12 wherein said linker arm comprises a double bond at an α (alpha) position relative to the base.

14. The method of claim 13 wherein said linker arm is selected from the group consisting of

—CH=CH—CH$_2$—NH—,

—CH=CH—CH$_2$—S—, and

—CH=CH—CH$_2$—O—CH$_2$—CH$_2$—NH—.

15. The method of claim 14 wherein said linker arm comprises allylamine.

16. The method of claim 15 wherein said allylamine is attached to the 5-position of uracil.

17. The method of claim 11 wherein said linker arm is attached to the base moiety in one fragment.

18. The method of claim 11 wherein said linker arm is synthesized by first attaching a first fragment to the base moiety and then attaching a second fragment to the first fragment.

19. The method of claim 11 wherein said base is selected from the group consisting of purines, pyrimidines and deazapurine, or a combination of any of the foregoing.

20. The method of claim 19 wherein said purine comprises adenine or guanine, and wherein said linker arm is attached to the 8-position or exocyclic 6-amino position when said purine comprises adenine, or to the 8-position when said purine comprises guanine.

21. The method of claim 19 wherein said base comprises a deazapurine, and wherein said linker arm is attached to the 7 or 8-position.

22. The method of claim 19 wherein said pyrimidine comprises uracil or cytosine, and wherein said linker arm is attached to the 5 or 6-position when said pyrimidine comprises uracil, or at the 5, 6, or exocyclic 4-amino position when said pyrimidine comprises cytosine.

23. The method of claim 1 wherein said diazonium salt comprises 4-nitrobenzenediazonium salt.

24. The method of claim 23 wherein said 4-nitrobenzenediazonium salt is halogen-substituted.

25. The method of claim 24 wherein said halogen-substituent comprises chlorine and bromine, or a combination thereof.

26. The method of claim 25 wherein said chlorine substituted 4-nitrobenzenediazonium salt is selected from the group consisting of 3-chloro-4-nitrobenzenediazonium salt, 3,5-dichloro-benzenediazonium salt, 2,6-dichloro-benzenediazonium salt, 2,3,5,6-tetrachloro-benzenediazonium salt, 3,5,6-trichloro-benzenediazonium salt, 2,3,5-trichloro-benzenediazonium salt and 2,3,6-trichloro-benzenediazonium salt, or a combination of any of the foregoing.

27. The method of claim 1 further comprising the step of adding an inactivator which renders said inactivating reagent inactive prior to detecting the signal.

28. The method of claim 27 wherein said inactivator is selected from the group consisting of an aliphatic primary amine, a phenol and an aromatic amine, or a combination of any of the foregoing.

29. The method of claim 28 wherein said aliphatic primary amine is selected from the group consisting of glycine, alanine, arginine, asparagine, aspartic acid, cysteine, cystine, glutamic acid, glutamine, histidine, hydroxylysine, isoleucine, leucine, lysine, methionine, serine, threonine and valine, or a combination of any of the foregoing.

30. The method of claim 29 wherein said aliphatic primary amine comprises glycine.

31. A method of detecting the presence of a polynucleotide of interest comprising the steps of:

(a) contacting a sample suspected of containing said polynucleotide of interest with (i) a single-stranded polynucleotide probe, said polynucleotide probe comprising a polynucleotide and at least a first intercalating aromatic dye and a second intercalating aromatic dye, wherein said first intercalating aromatic dye is attached to a first nucleotide of said polynucleotide by means of a first linker arm, and said second intercalating aromatic dye is attached to a second nucleotide by means of a second linker arm, said first and second nucleotides being separated by a number of nucleotides sufficient for providing specificity to said polynucleotide of interest, said intercalating aromatic dye inducing upon hybridization of said polynucleotide probe to said polynucleotide of interest a change in a property either in the polynucleotide probe, the polynucleotide of interest, or in both; and (ii) an inactivating reagent which chemically modifies and inactivates said intercalating aromatic dyes when the probe attached thereto is single-stranded;

(b) forming a hybrid comprising said polynucleotide probe and said polynucleotide of interest; and (c) detecting the presence of said polynucleotide of interest by means of said property change, wherein said intercalating aromatic dye is selected from the group consisting of phenanthridine, acridine, and a combination thereof, said inactivating reagent comprises a diazonium salt, and said property change is a change in radiation emission.

32. A nucleic acid hybridization kit for detecting the presence of a polynucleotide of interest, said kit comprising in one or more containers:

(1) a single-stranded polynucleotide probe which is hybridizable to said polynucleotide of interest, said probe comprising a polynucleotide and at least one intercalating aromatic dye attached to a nucleotide of said polynucleotide by means of a linker arm, wherein said intercalating aromatic dye induces a change in a property in either said probe, said polynucleotide of interest, or both;

(2) an inactivating reagent which chemically modifies and inactivates said intercalating aromatic dye when the probe attached thereto is single-stranded, wherein said intercalating aromatic dye is selected from the group consisting of phenanthridine, acridine, and a combination thereof, said inactivation reagent comprises a diazonium salt, and said property change is a change in radiation emission; optionally with (3) an inactivator which renders inactive the inactivation reagent itself.

33. A composition comprising a single-stranded polynucleotide probe having at least one moiety with the structure

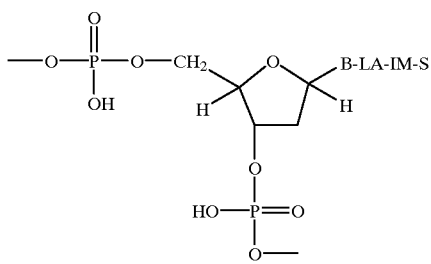

wherein B represents a base selected from the group consisting of pyrimidines, purines, and deazapurines, provided that whenever B comprises a pyrimidine, the sugar in said base is attached to the $N^1$-position of the pyrimidine, and whenever B is a purine or a deazapurine, the sugar is attached to the $N^9$-position of the purine or deazapurine, wherein IM represents an intercalating aromatic dye, LA represents a linker arm comprising at least three carbon atoms and is attached covalently or non-covalently to said intercalating aromatic dye, and S represents an inactivating reagent which chemically modifies and inactivates said intercalating aromatic dye when the probe attached there is single-stranded; wherein said intercalating aromatic dye is selected from the group consisting of phenanthridine, acridine, and a combination thereof, and said inactivation reagent comprises a diazonium salt.

34. The composition of claim 33 wherein said purine comprises adenine or guanine, and wherein said linker arm is attached to the 8 or the exocyclic 6-amino position when said purine is adenine, or at the 8-position when said purine is guanine.

35. The composition of claim 33 wherein said pyrimidine comprises uracil or cytosine, and wherein said linker arm is attached to the 5 or 6 position when said pyrimidine is uracil, or at the 5, 6 or exocyclic 4-amino position when said pyrimidine comprises cytosine.

36. The composition of claim 33 wherein said base comprises deazapurine and said linker arm is attached to the 7 or 8 position of said deazapurine.

37. The composition of claim 33 wherein said linker arm comprises a double bond at an α (alpha) position relative to the base.

38. The composition of claim 37 wherein said linker arm is selected from the group consisting of

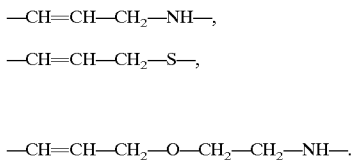

and

—CH=CH—CH$_2$—O—CH$_2$—CH$_2$—NH—.

39. The composition of claim 38 wherein said linker arm comprises allylamine.

40. The composition of claim 39 wherein said allylamine is attached to the 5-position of uracil.

41. The composition of claim 33 wherein said linker arm is attached to said base in one fragment.

42. The composition of claim 33 wherein said linker arm is synthesized by first attaching a first fragment to said base and then attaching a second fragment to said first fragment.

43. The composition of claim 33 wherein said aromatic dye comprises a phenanthridine.

44. The composition of claim 43 wherein said phenanthridine is selected from the group consisting of ethidium, propidium, dimidium and phenidium, or a combination of any of the foregoing.

45. The composition of claim 44 wherein said propidium comprises 5-(4'-thiobutyl)-3,8-diamino-6-phenylphenanthridine or 5-(3'-thiopropyl)-3,8-diamino-6-phenylphenanthridine, or a combination thereof.

46. The composition of claim 44 wherein said phenanthridine comprises ethidium.

47. The composition of claim 33 wherein said acridine comprises acridine orange.

48. The composition of claim 33 wherein said diazonium salt comprises a 4-nitrobenzenediazonium salt.

49. The composition of claim 48 wherein said 4-nitrobenzenediazonium salt is substituted by a halogen selected from chlorine and bromine, or a combination thereof.

50. The composition of claim 49 wherein said chlorine-substituted 4-nitrobenzenediazonium salt is selected from the group consisting of 3-chloro-4-nitrobenzenediazonium salt, 3,5-dichloro-benzenediazonium salt, 2,6-dichloro-benzenediazonium salt, 2,3,5,6-tetrachloro-benzenediazonium salt, 3,5,6-trichloro-benzenediazonium salt, 2,3,5-trichloro-benzenediazonium salt and 2,3,6-trichloro-benzenediazonium salt, or a combination of any of the foregoing.

* * * * *